United States Patent
Galajda et al.

(10) Patent No.: US 9,743,916 B2
(45) Date of Patent: Aug. 29, 2017

(54) SURGICAL POSITIONING INSTRUMENT FOR SUPPORTING AND HOLDING ORGANS

(71) Applicant: Aesculap AG, Tuttlingen (DE)

(72) Inventors: Zoltan Galajda, Debrecen (HU); Dominik Seyfried, Königsfeld (DE); Theodor Lutze, Balgheim (DE); Dieter Weisshaupt, Immendingen (DE); Thomas Beck, Durchhausen (DE); Sonja Verse, Rietheim-Weilheim (DE); Robert Vogtherr, Tuttlingen (DE); Andreas Elisch, Schramberg (DE); Pedro Morales, Tuttlingen (DE); Omer Dzemali, Zürich (CH); Lajos Patonay, Budapest (HU)

(73) Assignee: AESCULAP AG (DE)

( * ) Notice: Subject to any disclaimer, the term of this patent is extended or adjusted under 35 U.S.C. 154(b) by 0 days.

(21) Appl. No.: 14/652,933

(22) PCT Filed: Dec. 19, 2013

(86) PCT No.: PCT/EP2013/077482
§ 371 (c)(1),
(2) Date: Jun. 17, 2015

(87) PCT Pub. No.: WO2014/096252
PCT Pub. Date: Jun. 26, 2014

(65) Prior Publication Data
US 2015/0335323 A1    Nov. 26, 2015

(30) Foreign Application Priority Data
Dec. 20, 2012    (DE) .................. 10 2012 112 787

(51) Int. Cl.
A61B 1/32    (2006.01)
A61B 17/00    (2006.01)
(Continued)

(52) U.S. Cl.
CPC .... *A61B 17/00234* (2013.01); *A61B 17/0218* (2013.01); *A61B 17/02* (2013.01);
(Continued)

(58) Field of Classification Search
CPC ........ A61B 2017/0243; A61B 17/0293; A61B 1/32; A61B 2017/0212;
(Continued)

(56) References Cited

U.S. PATENT DOCUMENTS 4,637,377 A    1/1987 Loop
5,453,078 A    9/1995 Valentine
(Continued)

FOREIGN PATENT DOCUMENTS

EP    1002498    5/2000
EP    1028656    12/2008
WO    9920321    4/1999

OTHER PUBLICATIONS

German Search Report for German Application No. 10 2012 112 787.5 mailed Sep. 5, 2013, including partial translation.
(Continued)

*Primary Examiner* — Lynnsy Summitt
(74) *Attorney, Agent, or Firm* — Ratnerprestia

(57) ABSTRACT

A surgical positioning instrument for supporting and holding organs includes a preferably concave bearing portion and a supporting portion substantially rearward with respect to the bearing portion. Via the bearing portion an organ which is to be positioned can be received and via the supporting portion the surgical positioning instrument can be supported at an environment of the organ. Further, at least the bearing portion partly simulates a surface of the organ to be supported and is designed to be dimensionally stable.

13 Claims, 3 Drawing Sheets

(51) Int. Cl.
  *A61B 17/02* (2006.01)
  *A61B 17/30* (2006.01)
(52) U.S. Cl.
  CPC ........... *A61B 2017/00075* (2013.01); *A61B 2017/00243* (2013.01); *A61B 2017/0243* (2013.01); *A61B 2017/306* (2013.01); *A61B 2217/005* (2013.01)
(58) Field of Classification Search
  CPC ....... A61B 2017/320048; A61B 2017/320044; A61B 2017/0237; A61B 17/0218; A61B 17/02; A61B 2017/00557; A61B 2017/0225; A61B 2017/306; A61B 17/0281; A61B 2017/00243; A61B 2017/308; A61B 17/00234
  See application file for complete search history.

(56) References Cited

U.S. PATENT DOCUMENTS

| | | | |
|---|---|---|---|
| 5,735,791 A | 4/1998 | Alexander, Jr. | |
| 6,036,640 A | 3/2000 | Corace | |
| 6,447,443 B1* | 9/2002 | Keogh | A61B 17/0206 128/898 |
| 6,506,149 B2* | 1/2003 | Peng | A61B 17/02 600/201 |
| 6,641,575 B1* | 11/2003 | Lonky | A61B 17/00234 600/210 |
| 6,899,670 B2 | 5/2005 | Peng | |
| 6,988,984 B2* | 1/2006 | Parsons | A61B 17/02 600/201 |
| 7,438,680 B2 | 10/2008 | Guenst | |
| 7,479,104 B2* | 1/2009 | Lau | A61B 17/0206 600/37 |
| 7,494,460 B2* | 2/2009 | Haarstad | A61B 17/00234 600/37 |
| 2002/0095139 A1* | 7/2002 | Keogh | A61B 17/0206 606/1 |
| 2002/0115911 A1* | 8/2002 | Knight | A61B 17/02 600/228 |
| 2003/0078471 A1* | 4/2003 | Foley | A61B 17/02 600/37 |
| 2003/0139646 A1* | 7/2003 | Sharrow | A61B 17/02 600/37 |
| 2004/0138522 A1 | 7/2004 | Haarstad | |
| 2005/0203334 A1* | 9/2005 | Lonky | A61B 17/00234 600/37 |
| 2006/0041243 A1 | 2/2006 | Nayak | |
| 2011/0144438 A1 | 6/2011 | Paolitto | |

OTHER PUBLICATIONS

International Search Report for International Application No. PCT/EP2013/077482 mailed Mar. 25, 2014.

* cited by examiner

SURGICAL POSITIONING INSTRUMENT FOR SUPPORTING AND HOLDING ORGANS

RELATED APPLICATIONS

This application is the United States national phase entry of International Application No. PCT/EP2013/077482, filed Dec. 19, 2013, which claims the benefit of priority of German Application No. DE 10 2012 112 787.5, filed Dec. 20, 2012. The contents of International Application No. PCT/EP2013/077482 and German Application No. DE 10 2012 112 787.5 are incorporated by reference herein in their entireties.

FIELD

The invention relates to a surgical positioning instrument for supporting and holding organs.

BACKGROUND

During surgery on organs such as on the heart it is necessary to at least temporarily position the organ. This is important, on the one hand, so that the site of operation of the organ is easily accessible for the operating surgeon. Moreover, especially sensitive organs, as it is the case especially with the heart, must not move during the surgical intervention. Therefore most different technologies and devices for positioning organs during an operation are known.

Organs can be supported and held, respectively, solely by the human hand or with the aid of instruments such as surgical hooks. It is a drawback that in this way an unevenly distributed pressure is exerted on the organ. Furthermore, a position cannot be permanently fixed, especially because the human hand fatigues comparatively quickly and starts twitching. Moreover it constitutes a major visual obstruction.

When drapes are laid underneath, at least the sight of the operating surgeon is unhindered. However, also in this case neither a comfortable nor a permanent positioning is ensured, because the drapes continuously absorb moisture and thus are losing stability. Moreover, the insertion of drapes until the desired position is reached is also time-consuming.

From EP 1 002 498 A1, U.S. Pat. Nos. 5,735,791 A and 6,036,640 A inflatable positioning cushions are known, and from U.S. Pat. No. 4,637,377 A and EP 1 028 656 B1 inflatable wedges are known, wherein the latter document works with a plurality of separate fluid chambers. All of these subject matters are based on the fact that they are put underneath the relevant organ and are subsequently inflated or filled with fluid.

It is a drawback of these systems that they do not take sufficient account of the anatomic conditions of the organs and consequently are not comfortable. Further the non-fitting form results in the fact that the organs have to be clamped, especially in the case of the wedge, and in this way local pressure sores are occurring at the organ, which entails increased hematoma formation. In addition, the hemodynamics of the heart is restricted.

From U.S. Pat. Nos. 6,899,670 B2 and 7,438,680 B2 additionally vacuum-assisted positioning systems are known. These systems substantially consist of a frame to be assembled in advance comprising an arm or jointed arm by which a suction member is mounted on the frame and is positioned at the organ. Moreover, a vacuum pump generates a relative vacuum which is transmitted to the suction member by means of a complicated pressure monitoring apparatus. The suction member sucks the organ and in this way positions the same. It is a drawback that these systems are very bulky. Furthermore they require great mounting efforts before surgery can be started after positioning the organ. Also they are cost-intensive.

The patent document U.S. Pat. No. 5,453,078 A discloses a wedge-shaped sponge means comprising a stiff and absorptive sponge member. The sponge is preferably used to either render the organ to be operated on accessible by pushing organs that bar the way to the side or bringing the organ to be operated on into the operating area. During use the wedge-shaped sponge is clamped between the organs so that upon increasing absorption of moisture it appropriately expands by a multiple of its initial size and clamps the organs.

It is a drawback in this case that the initially stiff sponge exerts an uneven and usually substantially point-shaped pressure distribution on the organ, which is not comfortable and causes hematomas. In addition, an uncomfortable support restricts the hemodynamics of the heart.

In addition, the wedge is brought into a favorable and stable position by trying out so that both the organ is positioned in the desired way and the wedge is safely clamped. This step is time-consuming and even in such case it cannot be excluded that the wedge may come loose again at any time.

Moreover, in the course of continuous soaking of the sponge the state of positioning is continuously varied. It is continuously transformed from a wedged state into a state receiving and partly enclosing the organ. Since in this case the entire pressure distribution changes both between the organ and the sponge and between the sponge and the bearing face, also the positioning of the organ necessarily varies. Accordingly, increasing absorption of moisture is accompanied by decreasing stability of positioning.

SUMMARY

Compared to this, it is the object of the invention to provide a positioning instrument that is most universally applicable as regards the size of the organ for reliably receiving and holding organs, wherein the function of the organ is adversely affected as little as possible.

This object is achieved by a surgical positioning instrument as described herein.

The surgical positioning instrument according to the invention (hereinafter referred to as instrument) for supporting and holding organs comprises on one side face a concave bearing portion by which an organ can be received. At its side face rearward with respect to the bearing portion the instrument has a supporting portion by which it can be supported at the environment of the organ. A surface of the bearing portion is substantially adapted to an outer surface, especially a shell or a shell surface of the organ to be positioned and simulates the latter in a dimensionally stable manner so that by the most ideal fit it supports and permanently holds the organ while the pressure is evenly distributed over the bearing face.

It is furthermore beneficial that the dimensionally stable instrument can be quickly positioned without an additional fixation by means of drape underlays and loops or tensioning cords to the environmental tissue being required.

The ideal fit is of particular advantage to the effect that it prevents vital vessels and/or vessel structures at the organs from being occluded. In particular in the case of the heart this advantage is important, because thus the hemodynamics of the heart is not restricted.

It is a beneficial effect of the adapted and dimensionally stable bearing portion that the effort of mounting and positioning is minimized especially at the beginning of surgery until the actual operation on the organ concerned can be started.

In an especially preferred embodiment the instrument can be a substantially wedge-shaped heart pad adapted to be inserted in the pericardial cavity of the heart. The bearing surface of the heart pad most closely simulates, at least in portions, a surface contour of the heart.

The wedge shape of the heart pad tapered in the inserting direction permits easy insertion into the pericardial cavity. The heart is received by the concave bearing portion of the heart pad so that the epicardium and the bearing portion contact each other, while the heart pad rests on the pericardium via the rear supporting portion of preferably convex shape.

The surface of the bearing portion simulates the surface contour of the heart at least in the area where it contacts the heart. Thus the heart pad is capable of perfectly supporting and holding the heart by the bearing face having the negative shape of the heart.

The ideal fit of the heart pad along with the wedge shape in the inserting direction as well as in a depth direction of the heart pad perpendicular thereto offers the special advantage that the heart pad is retained in the desired position in the pericardial cavity without any additional fixation. This is achieved in that the epicardium and the pericardium are tensioned by insertion of the heart pad and in this way are positioning the heart.

It is another advantage that no bulky and complex apparatuses are required for fixing the heart pad and thus an operating surgeon's free view is further not obstructed.

The simple design entails a clear cost advantage as well as a reduced mounting effort. In addition, by omission of the mounting apparatus valuable time as regards the patient's health and cost-intensive time as regards the duration of surgery can be saved in that the heart is positioned more rapidly.

In order to immobilize an operating site, in a preferred embodiment the heart pad can have an integrated sensor-actuator combination. In this case the sensor detects a heat movement and based on a result of detection of the sensor an actuator generates a pulse to minimize a relative movement between the heart and the heart pad.

It is an advantage of the balance of movement that the heart can continue beating unhindered and at the same time the operating surgeon is provided with a largely immobilized operating site. In addition, this embodiment does not restrict the hemodynamics of the heart.

Alternatively or in addition to the sensor-actuator combination, the material of the heart pad can exhibit, at least in partial areas, especially good damping material properties so as to absorb the kinetic energy of the heart.

According to an especially preferred development, the instrument can have recesses in accordance with the anatomic conditions of the organ.

Said recesses introduced in a specific manner offer the advantage that areas projecting from the organ such as blood vessels or the like can be received by the recesses such that the full surface of the residual organ can be supported and held by the bearing face. In this way neither hematomas are formed due to substantially point-shaped load nor are vital vessels and/or vessel structures occluded or adversely affected in any way. Additionally, the function of the organ, in the case of the heart the hemodynamics, is thus not restricted.

Solely by their striking form the recesses can prevent the instrument from being wrongly arranged. In addition or alternatively, the instrument can be provided with preferably permanently arranged instructions or markings illustrating an intended purpose of the respective recess so that the instrument can be correctly used.

In order to be able to insert and remove the instrument during operation in a simple and rapid manner it can furthermore exhibit a portion preferably being arranged at the proximal end and being designed as a mounting and removing aid. Said portion preferably is in the form of at least one eye or loop at which the instrument can be seized or caught.

Advantageously the portion is configured so that it can be caught and guided with the aid of an instrument provided in every perforated basket. Thus the instrument can be manipulated without the help of the hand. This is especially advantageous, because merely sliding of the instrument by the hand or by a finger is possible by means of simple contact. Any other movement such as removal or pulling as well as any rotation of the instrument requires the latter to be seized by the hand with at least two fingers. Thus comparatively large space is required at the organ which usually is not provided.

In contrast to this, the mounting and removing aid permits the instrument being seized at its proximal end and being moved both translationally and rotationally in any way.

Alternatively or in addition, the instrument can be provided especially at proximal portions with at least one auxiliary and/or holding device in the form of a loop, tab or the like to which preferably auxiliary sutures can be attached. In this way neither further supports for backing the sutures necessary during surgery are required, nor have the sutures to be arranged at the surrounding tissue and thus damage the latter.

The afore-described fixing aids may be provided at one or more surfaces of the instrument such as a heart pad. In the event of critical surgery, it may be necessary to additionally fix the instrument according to the invention by holding sutures. In this case fixing aids may also be provided on distal surfaces of the instrument into which initially a fixation thread is threaded which, after inserting the instrument into the final position, is completed to form the holding suture.

In order to be able to suck fluids off the operating site, the instrument furthermore can comprise a discharge device having at least one passage in the form of a drain passage and/or an air resupply passage. The instrument can be formed especially such that into a passage preferably having a polygonal cross-section a further passage having a cross-sectional shape different therefrom is introduced. In this manner one part of the overall cross-section can serve for discharging a fluid while the other part serves for resupplying air.

The discharge device serves for the discharge of fluids. Especially in the pericardial cavity surrounding the heart pad fluid from the pericardial space is present which can be discharged by means of a passage. Preferably a distal end of the passage is arranged in the vertical direction approximately at a position of the heart pad lowermost in the inserted state, and a proximal end of the passage is arranged approximately at a position of the instrument opposed to the lowermost position. The proximal end can be connected to a suction means such as a hand suction pump, a manual suction pump (actuated by foot) and/or an electrically actuated suction pump or an aspirator.

In a further development the discharge device can be designed, instead of a passage for discharging fluids as well as for supplying air, to alternatively or additionally include at least one discharge passage or suction passage in the form of a drain passage and at least one air passage in the form of an air supply passage.

Preferably the connection of the discharge device is materialized via a simple and universal connecting system such as the Luer system (Luer socket, lock, plug, slip) to a suction means.

In order to prevent tissue from being sucked at a suction orifice of the discharge passage, furthermore a venting system can be integrated such that a recess at which at least one air passage terminates is provided in the heart pad at the distal end portion of the discharge device. In this way air can flow in corresponding to the suction volume so as to prevent the suction orifice from being partly or completely closed or blocked.

Furthermore, the area of the suction orifice can be configured so that the suction passage is reset at its distal end in the proximal direction relative to the recess so that the distal end thereof does not project from the heart pad. In addition, braces or a grid-like structure can be provided in the area of the recess for preventing contact between the tissue and the suction passage. It is noted that the contact can only be prevented when a positive distance is constantly maintained between the distal end portion of the suction passage and the grid-like structure.

By the described discharge device free fluids such as liquid blood, effusion fluid or the like consequently can be directly and easily discharged without the actual operation having to be interrupted in order to use a sponge, aspirator etc.

Alternatively or in addition to the discharge device, the heart pad can consist entirely or partly of absorptive material. In this way the fluid occurring during surgery is absorbed directly and so-to-speak automatically, wherein the discharge device can be used in an assisting function.

It is expressly noted in this context that the afore-mentioned discharge means is not restricted to the heart pad but can equally be applied to any other surgical positioning instrument according to the invention. Also, the discharge device need not necessarily be a physical part of the surgical instrument but can also be inserted into the surgical instrument from outside.

With an increasing duration of surgery organs are increasingly cooling. To counteract this phenomenon, the instrument can include heat-insulating material at least at the bearing portion so as to avoid excessive loss of heat of the organ. Additionally or alternatively, a thermal element can be provided preferably inside the instrument so as to supply heat to the organ if required.

In a further development suction cups and/or vacuum segments can be provided as fixation means at a desired position of the instrument. A relative vacuum between the suction cups and an environment such as the organ or the like can be obtained, for example, by pressing down the suction cups. Likewise a vacuum source can be used which is connected to the suction cups so that it is adapted to suck off air between the suction cups adjacent to the organ and the organ so as to fix the instrument to the organ in this way.

On the one hand, said fixation means is suited for fixing the organ concerned to the surgical instrument. In addition or as an alternative, the fixation means can be used to locally fix the surgical instrument to the environment.

Therefore the fixation means is especially advantageous in an operation on the heart. In this case the heart pad for fixing and positioning the heart is inserted into the pericardial cavity. Suction cups provided at the bearing portion fix the heart via the epicardium and hold it at the desired position relative to the heart pad, while suction cups provided at the supporting portion fix the heart pad at the pericardium and thus hold it at the desired position relative to the patient. In this way the heart pad can be brought exactly into the position at which the operating surgeon has unobstructed access to the desired site of the heart and can be permanently held there.

In order to additionally prevent slipping between the organ and the instrument and the surrounding tissue, respectively, the surface at the bearing portion and at the supporting portion, resp., can preferably be provided with a mesh, a textile coating or the like. This embodiment is especially advantageous when the surface coating is moreover absorptive so that a possible greasy film is absorbed. Moreover, this allows that fluids are directly absorbed during surgery so that they need not be sucked off and discharged.

In order to further improve the capability of movement and positioning the instrument may exhibit a plurality of fluid chambers adapted to be individually filled. The volume of the respective chambers can be continuously varied individually from outside. By interaction of the different chambers the operating surgeon has the possibility of easily and efficiently manipulating so as to vary the position of the organ in the course of the operation and to be able to perform a fine adjustment. In particular a system made of plural chambers turns out to be of advantage to the effect that neither the operating surgeon nor any assistant instructed by the operating surgeon has to move and repeatedly fix the organ directly by his/her hand but can conveniently do so via filling and/or emptying the fluid chambers.

The adaptability of the instrument to the organ and to the supporting face, respectively, can be further improved by the instrument including a soft portion preferably relating to the outer shell and a rigid portion preferably relating to the core. While the core adopts a major function in order to impart the required dimensional stability to the instrument, the soft outer skin serves for adapting to the conditions of its contact surface. It is especially advantageous when a viscoelastic outer skin is used.

As an alternative, the instrument may include a shell the bearing portion and/or supporting portion of which is filled with granular powder. From the shell the air contained in the same can be removed via a valve, for example. Consequently, the shell permits better adaptability of an outer skin of the instrument to each patient. This is achieved in that at first the adaptable outer skin of the instrument can adapt to the shape of the organ or of the supporting environment. When the optimum shape is reached, a relative vacuum is generated in said shell so that the individual granular particles are pressed against one another and the outer skin becomes rigid and the current positioning is maintained. In this way the adaptability of the instrument can be even further improved.

In an especially preferred development the instrument can be a system of modular structure. In this context, in particular a two-part system is reasonable in which bearing portions and supporting portions having different dimensions, shapes and configurations can be combined.

What is also possible is a module in the form of an air cushion adapted to be integrated in the instrument. Thus the operating surgeon can navigate the heart during surgery by filling and emptying the air cushion with a fluid.

In this way the instrument can be adapted individually to each patient, whereby the organs can be supported and positioned even better and drawbacks such as hematomas, restricted hemodynamics of the heart and the like can be more efficiently prevented.

Moreover, additional elements such as suction cups and device members either with or without a textile coating, mounting aid, holding device and the like can be individually composed so as to obtain an instrument for positioning organs which is optimally tailored to the patient.

It is further advantageous that defective or worn parts can be exchanged without the entire instrument having to be replaced. Alternatively, at least some of the parts can be disposable parts.

BRIEF DESCRIPTION OF THE DRAWING FIGURES

Hereinafter preferred embodiments of a surgical instrument according to the invention for supporting and holding organs shall be illustrated in detail with reference to the enclosed drawings.

DETAILED DESCRIPTION

Figure 1:
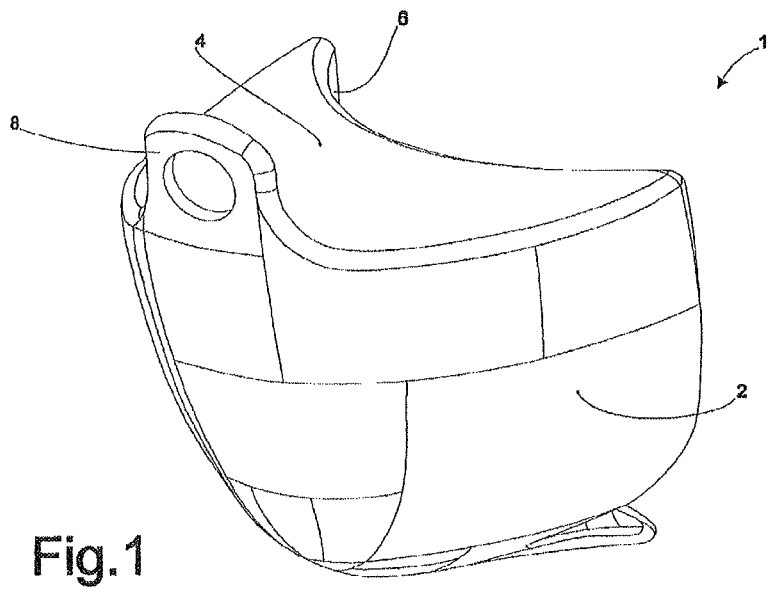
FIG. 1 shows a schematic perspective representation of a surgical instrument in a back view according to a first embodiment of the invention.

FIG. 1 exemplifies in a perspective view a heart pad 1 as a surgical instrument for positioning organs. It is noted that the upper side in FIG. 1 corresponds to a lower side of the heart pad 1 in the inserting direction. The heart pad 1 substantially consists of three surfaces. A surface denoted with the reference numeral 4 serves as lower side face 4 and is approximately in the form of a semi-ellipse. A secondary ellipse axis constitutes a base side of the lower side face 4, wherein the latter is curved so that the lower side face 4 is reduced compared to a straight elliptical conjugate axis.

It would be equally possible that the base side extends in an opposite direction such that the lower side face 4 is enlarged.

A bearing portion 6 which is arranged substantially in the inserting direction normal to the surface 4 is connected to the elliptical conjugate axis of the lower side face 4 via a rounded edge.

A supporting face 2 or bearing face which serves as rear side of the heart pad 1 and by which the heart pad 1 rests on an environment is connected to the other edge of the lower side face 4 via a rounded edge. The supporting face 2 is a rounded convex outer shell surface and has a maximum sectional diameter on the side toward the lower side face 4, whereas the sectional diameter decreases toward the other end (in the inserting direction). In other words, the supporting face 2 substantially corresponds to an end portion of a rounded trough forward in the longitudinal direction.

An element in the form of an eye or a loop toward which the supporting face 2 expands in portions at the crest of the semi-ellipse and projects approximately perpendicularly to the lower side face 4 serves as a mounting and removing aid 8. The mounting and removing aid 8 can also be provided in the form of a recess in the outer skin of the heart pad 1 at which a stud is formed for seizing the heart pad 1.

As is evident from FIG. 1, the heart pad 1 has at its lower side maximum dimensions both as to width and as to depth, whereas it is tapered in the direction of the upper side with which the heart pad 1 is inserted forward into a pericardium. In this way a substantially wedge-shaped configuration is realized so that through the front area tapering in the inserting direction the heart pad 1 can be inserted more easily into the pericardial cavity. At the same time, the heart pad 1 can be better clamped between the pericardium and the epicardium by the more bulky area at the rear in the inserting direction.

Of preference, the heart pad 1 is guided by an instrument present in each perforated basket such as forceps or the like (not shown) via the mounting and removing aid 8.

Figure 2:
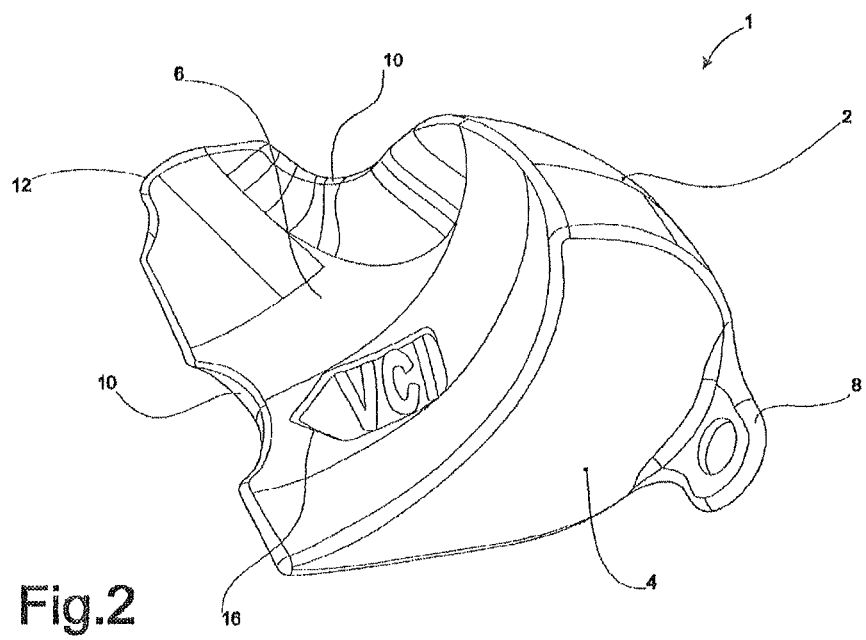
FIG. 2 shows the surgical instrument according to FIG. 1 in a front view.

FIG. 2 is a perspective representation of the heart pad 1 of FIG. 1 in which a front side of the heart pad 1 is evident. The front side includes a bearing portion 6 in the form of a rounded concave surface. The bearing portion 6 simulates a surface of the heart in a dimensionally stable manner and consequently constitutes a negative form to the heart surface. As a consequence, the heart (not shown) can be supported and held by the bearing portion 6 that is optimally tailored to the heart contour. In the ideal case the bearing portion 6 and the outer skin of the heart constitute two corresponding surfaces that are matching almost perfectly.

Furthermore, at border areas the bearing portion 6 is provided with recesses 10 along the respective edge between the bearing portion 6 and the supporting face 2. Said recesses are preferably arranged at the locations where, in the inserted condition of the heart pad 1, vital and distinct vessels and/or vessel structures are provided. In accordance with the respective vessel or the respective vessel structure which is received by the trough-shaped recess 10, the latter has a larger, smaller or non-uniform radius. In this case the depth as well as the width and the number of recesses 10 can be varied.

The wedge shape of the heart pad 1 is also found in the bearing portion 6. The latter has its maximum width at the one end portion on the side of the lower side face 4 and becomes increasingly narrower in the inserting direction of the heart pad 1. At the other end portion of the bearing portion 6 the latter is transformed into a front portion 12 of the bearing face which constitutes a wedge point. The latter can be symmetric or asymmetric. Furthermore, the wedge point 12 can be centered as well as offset in the longitudinal direction with respect to the bearing portion 6 so that the heart pad 1 can be inserted into the pericardial cavity at minimum resistance and can be passed by and placed between vessels where appropriate.

The heart pad 1 further includes a marking 16 on the surface of the bearing portion 6. Said marking is labeled and exhibits an arrow so that the operating surgeon can unambiguously recognize at which orientation the heart pad 1 has to be inserted. As is shown in FIG. 2, the label may denote concrete vessels such as the vena cava inferior, for instance. It may also include other information such as an orientation of the heart pad 1 relative to the patient's body.

Figure 3:
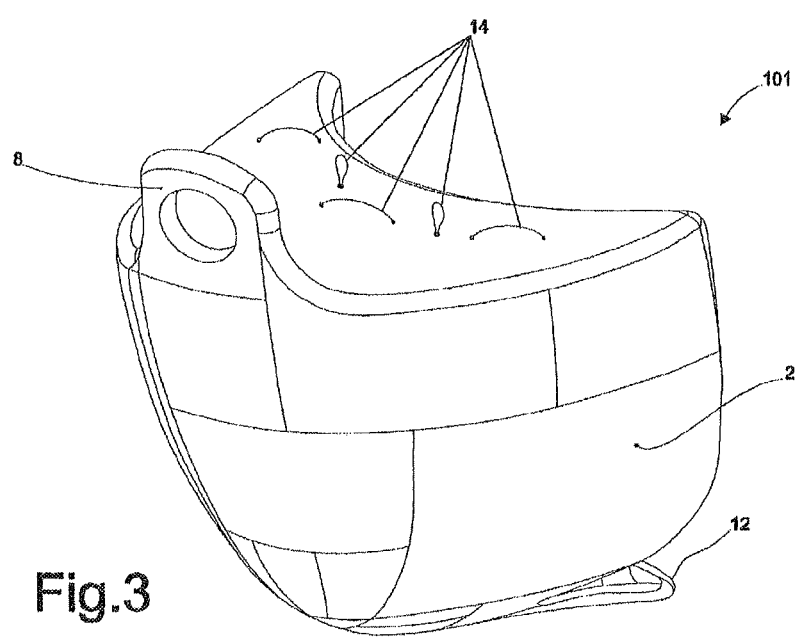
FIG. 3 shows a schematic perspective representation of a surgical instrument in a back view according to a second embodiment of the invention.

In FIG. 3 a schematic perspective representation of a heart pad 101 is shown in a back view according to a second embodiment of the invention. The second embodiment differs from the first embodiment in that it additionally includes at least one and preferably plural auxiliary and holding devices 14 arranged at the lower side face 40. The auxiliary and holding devices in the form of loops 14 at approximately regular intervals are especially suited for arranging auxiliary and holding sutures that are temporarily required during surgery. The loops 14 can equally be provided on other surfaces of the heart pad.

Furthermore, instead of loops also tabs provided with eyes (not shown) can be used. The latter offer the additional advantage that they are adjacent to and flush with the respective surface and can be folded up if required. Alternatively or in addition, trough-shaped recesses can be provided in the surface of the heart pad, wherein at least one land to which sutures can be fastened is present in the recesses.

Figure 4:
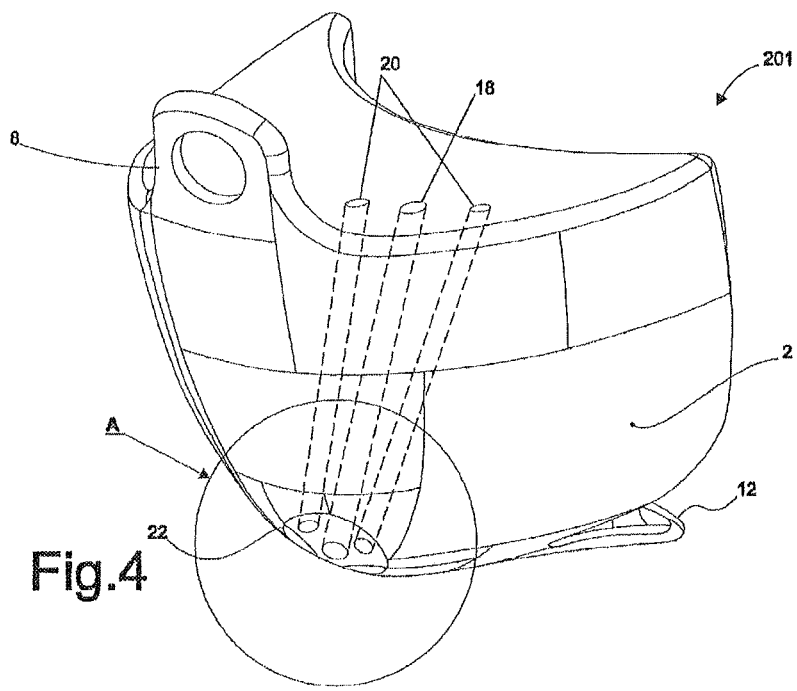
FIG. 4 shows a schematic perspective representation of a surgical instrument in a back view according to a third embodiment of the invention.

FIG. 4 illustrates a schematic perspective representation of a heart pad 201 in a back view according to a third embodiment of the invention. By means of the transparent representation of the heart pad 201 passages 18, 20 extending in the same are evident. At least one passage serves as suction passage 18 for discharging free fluids from the site of operation. The suction passage 18 has a circular orifice at each of its two ends, the proximal orifice being provided at the lower side face 4 and the distal orifice being provided at a recess or suction orifice 22. The suction orifice 22 is introduced in the supporting face 2 in the area of the heart pad 201 which in the inserted condition is provided, in the case of a lying patient, at the substantially lowermost and farthest inserted position. In this way fluids collecting in the area that is most difficult to be reached by the operating surgeon can be discharged.

Apart from the suction passage 18, at least one further passage 20 serving as an air passage 20 for inflowing air is provided. The air passage 20 extends approximately in parallel to the suction passage 18. A proximal end is provided at the lower side face 4, while the distal end at the suction orifice 22 is provided as closely as possible to the distal orifice of the suction passage 18. For allowing sufficient air corresponding to the sucked off volume of the fluid to flow in through the suction passage 18 preferably two air passages 20 are provided, each of them having approximately the same diameter as the suction passage 18. In this way a relative vacuum, due to which the surrounding tissue is sucked and possibly covers the suction orifice 22, can be prevented from being generated in the suction area.

The suction passage 18 can optionally be connected at its proximal end to a hand suction pump, a manual suction pump (actuated by foot) and/or an electrically actuated suction pump or an aspirator. In order to ensure that air and not a fluid flows in through the air passages, also the latter can be connected at their proximal ends to any venting system. Preferably the connecting system used is the standardized Luer lock (not shown).

Instead of an external suction device, an internal suction device integrated in the heart pad 1 could be used.

Figure 5:
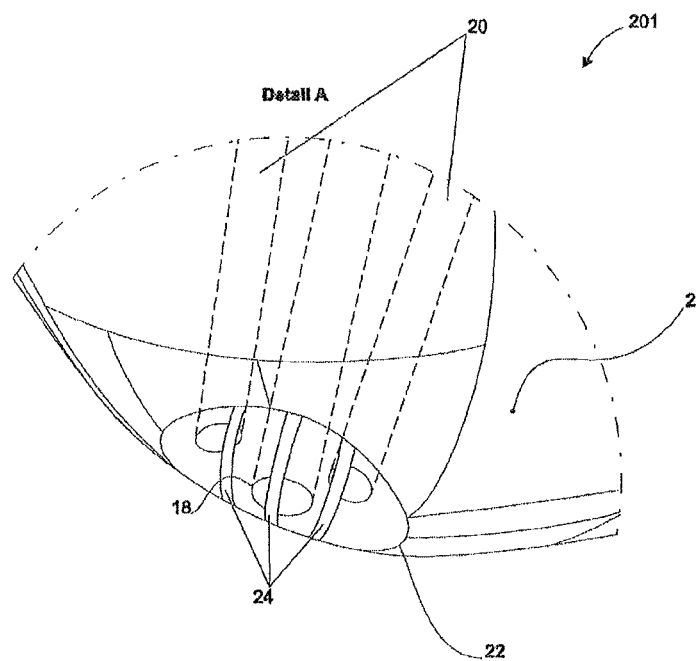
FIG. 5 shows a detailed view of a recess in FIG. 4.

FIG. 5 illustrates a detailed view of the suction orifice 22 in FIG. 4. It demonstrates that the passages 18 and 20 are slightly inwardly offset in the heart pad so that they do not project from the outer surface of the supporting face 2. Thus the surrounding tissue is prevented from being sucked. Furthermore, for an optimum inflow of air the suction passage 18 is partly surrounded by the air passages 20, wherein the respective distal ends thereof have to be arranged as closely to each other as possible.

Moreover, there are provided braces 24 arranged diametrically above the suction orifice 22 and preventing the tissue from being sucked by the distal orifice of the suction passage 18 and consequently from blocking the latter. The braces 24 preferably have a slightly curved shape so that they additionally space the tissue apart from the suction orifice 22.

Although in FIG. 5 three substantially vertically extending braces 24 are illustrated, the invention is not restricted thereto. Hence there can also be used more or fewer braces the orientation of which can be freely selected. Moreover a grid structure can be employed. When selecting the protective device care has to be taken that fluids can be discharged. In this context, it is important that, on the one hand, the orifice of the suction passage 18 is not blocked and, on the other hand, sufficient air flows in.

Deviating from the afore-described embodiments, the heart pad can be provided completely or partly, preferably at the lower side face 4 partly or completely with a fabric (not shown) in the form of a mesh or a textile coating. Auxiliary and holding sutures can be attached thereto in a simple manner. If plastic material having low tear propagation strength is used, sutures can be prevented from tearing.

Moreover, a fabric coating may equally be provided at the bearing portion and at the support portion, respectively, thereby slipping being suppressed and the positioning of the heart being enhanced. The same effect can be achieved by an appropriate surface texture. It may have an increased roughness and/or appropriately oriented scales.

Likewise combinations of the described embodiments are imaginable. The heart pad 201 according to the third embodiment may exhibit all features of the other embodiments, for example.

Of preference plastic material is considered as material, wherein also a metallic material or ceramics can be used. Especially preferred is a heat-insulating material that prevents excessive cooling.

Summing up, the core of the invention relates to a surgical instrument for positioning organs, especially hearts, which does not restrict the hemodynamics of the heart as well as the function of the respective organ and, at the same time, ensures an unobstructed view onto the organ for the operating surgeon. In this context, especially the comparable known solutions are taken into account which are either very bulky or unhandy and expensive and do not take the shape of the organs into consideration. The heart pad of the present invention positions the heart with little mounting effort in a low-cost manner especially by means of the ideal fit, while it does not restrict the hemodynamics of the heart. Since the heart pad is placed in the pericardial cavity and supports the heart individually and in any position, operations can be carried out on the back wall and on side walls of the heart. In this context, it is emphasized that the bearing faces are adapted to the heart and the environment thereof so that all sizes of hearts occurring can be positioned in a most ideal way.

The invention claimed is:

1. A surgical organ positioning instrument for supporting and holding organs during surgery comprising:
    a supporting portion having:
        a concave bearing surface portion by which a target organ to be surgically treated at a site of operation can be partially received;
        a convex supporting surface portion rearward with respect to the bearing surface portion by which the supporting portion can be freely supported at patient tissue surrounding the target organ; and a side face extending between the bearing surface portion and the supporting surface portion,
    wherein the bearing surface portion in addition to its concave shape at least partially simulates a surface of the target organ to be supported and is designed to be dimensionally stable in a permanent manner, and the supporting portion is wedge-shaped in an insertion direction as well as in a depth direction orthogonal thereto to be insertible into a pericardial cavity of a heart, wherein the bearing surface portion simulates a surface contour of the heart in a permanently dimensionally stable manner, wherein the supporting portion includes a discharge device comprising:

at least one passage in the form of a suction passage for discharging free fluids from a suction area, the suction passage extending through the side face; and apart from the suction passage, at least one further passage serving as an air passage for inflowing air to the suction area, the air passage extending through the side face and being adapted to allow air corresponding to a sucked volume of fluids to flow in through the air passage to prevent a relative vacuum from forming around tissue in the suction area, and wherein a proximal end of the suction passage is connected to a suction pump, and a proximal end of the air passage is connected to a venting system.

2. The surgical organ positioning instrument according to claim 1, wherein the supporting portion includes an integrated sensor-actuator combination in which electricity can be flowed for immobilizing the site of operation.

3. The surgical organ positioning instrument according to claim 1, wherein in the area of the bearing surface portion, the supporting portion is provided with at least one further recess or indentation at a surface thereof forming a support face adapted for large-scale support of body parts connected to the target organ, wherein the support face is adjacent to the bearing surface portion in a way expanding the bearing surface portion and is equally tailored to anatomic conditions of supported tissue.

4. The surgical organ positioning instrument according to claim 3, wherein the support face is oriented at an angle to the bearing surface portion, so that a ridge is formed between the support face and the bearing surface portion.

5. The surgical organ positioning instrument according to claim 3, wherein the supporting portion includes a heat-insulating material and/or a thermal element at least at the bearing surface portion and/or at the support face, wherein the heat-insulating material is an elastic material with a maximum heat conductivity of 1 W/(m*K).

6. The surgical organ positioning instrument according to claim 1, wherein the supporting portion further includes a gripping portion in the form of an eye or a loop by which the supporting portion can be arranged and/or removed via a surgical instrument.

7. The surgical organ positioning instrument according to claim 1, wherein the supporting portion includes an auxiliary and/or holding device to which auxiliary sutures can be attached.

8. The surgical organ positioning instrument according to claim 1, wherein the supporting portion includes a vacuum-based fixation device between the bearing surface portion and the target organ to be supported and/or between the supporting surface portion and the environment.

9. The surgical organ positioning instrument according to claim 1, wherein at least a surface area fraction of the bearing surface portion is provided with a mesh and/or textile coating.

10. The surgical organ positioning instrument according to claim 1, wherein the supporting portion includes a plurality of chambers adapted to be individually filled.

11. The surgical organ positioning instrument according to claim 1, wherein the supporting portion comprises an outer shell that forms a soft portion and a core that forms a rigid portion.

12. The surgical organ positioning instrument according to claim 1, wherein the supporting portion includes a shell which is filled with granular powder at least at the bearing surface portion and/or at the supporting surface portion, wherein air can be withdrawn from the shell.

13. The surgical organ positioning instrument according to claim 1, wherein the positioning instrument is a modular system.

* * * * *